United States Patent [19]

Fuchs et al.

[11] Patent Number: 5,264,571

[45] Date of Patent: Nov. 23, 1993

[54] PREPARATION OF CAPROLACTAM BY BECKMANN REARRANGEMENT OF CYCLOHEXANONE OXIME

[75] Inventors: Hugo Fuchs, Ludwigshafen; Gerald Neubauer, Weinheim; Josef Ritz, Ludwigshafen, all of Fed. Rep. of Germany

[73] Assignee: BASF Aktiengesellschaft, Ludwigshafen, Fed. Rep. of Germany

[21] Appl. No.: 954,731

[22] Filed: Sep. 30, 1992

[30] Foreign Application Priority Data

Sep. 30, 1991 [DE] Fed. Rep. of Germany ....... 4132498

[51] Int. Cl.$^5$ ................... C07D 201/04; C07D 201/16
[52] U.S. Cl. ..................................... 540/535; 540/540
[58] Field of Search ................................ 540/535, 540

[56] References Cited

U.S. PATENT DOCUMENTS

| | | | |
|---|---|---|---|
| 3,725,391 | 4/1973 | Suzuki et al. | 540/535 |
| 3,852,273 | 12/1974 | De Rooij | 540/535 |
| 3,953,438 | 4/1976 | Smith | 260/239.3 A |
| 4,072,678 | 2/1978 | Oyama et al. | 540/535 |
| 4,804,754 | 2/1989 | De Decker et al. | 540/540 |
| 4,806,638 | 2/1989 | Brand et al. | 540/540 |

FOREIGN PATENT DOCUMENTS 271014 4/1987 European Pat. Off. .

OTHER PUBLICATIONS

Derwent Abstract JA7339949 Dec. 29, 1970.

Primary Examiner—Mukund J. Shah
Assistant Examiner—Pavanaram K. Sripada
Attorney, Agent, or Firm—Keil & Weinkauf

[57] ABSTRACT

A process for preparing caprolactam by Beckmann rearrangement of cyclohexanone oxime with oleum at from 85° to 125° C. in a plurality of rearrangement stages arranged in series entails returning a portion of the reaction mixture leaving the last rearrangement stage to at least one of the preceding rearrangement stages.

4 Claims, No Drawings

PREPARATION OF CAPROLACTAM BY BECKMANN REARRANGEMENT OF CYCLOHEXANONE OXIME

The present invention relates to a process for preparing caprolactam by Beckmann rearrangement of cyclohexanone oxime with oleum in at least two rearrangement stages arranged in series.

Japanese Patent Publication 48/39949 discloses a process in which cyclohexanone oxime is reacted with oleum in a plurality of reaction zones arranged in series, with at least 70% of the oleum being fed into the first reaction zone, and the addition of cyclohexanone oxime being distributed over the individual reaction zones. In another process, which is described in U.S. Pat. No. 3,953,438, cyclohexanone oxime is reacted with oleum in two circulating zones arranged in series, with the major part of the cyclohexanone oxime being added in the first reaction zone and the minor part of the cyclohexanone oxime being added in the second reaction zone, and the total amount of oleum being fed into the first reaction zone. Although the prior art processes make it possible to reduce considerably the permanganate absorption number, it has emerged that the quality of the caprolactam no longer meets the increasingly strict quality requirements.

EP-A 271 014 has, moreover, disclosed a process in which the Beckmann rearrangement is carried out in a circulating system, and the resulting reaction mixture is subsequently left, without further addition of cyclohexanone oxime, in a holdup zone at 95° C. for 120 minutes. Although this succeeds in further improving the quality, it was not possible to reduce the oleum consumption. It is desirable in the Beckmann rearrangement of cyclohexanone oxime to caprolactam to keep the acid consumption as small as possible in order to minimize the unavoidable production of ammonium sulfate. However, as the ratio of oleum to cyclohexanone oxime decreases there is an increase in the risk of a deterioration in quality, especially in respect of UV-active compounds such as octahydrophenazine.

It is an object of the present invention to provide a process for preparing caprolactam by Beckmann rearrangement of cyclohexanone oxime with oleum, in which not only does the resulting caprolactam have a low permanganate absorption number, a low UV absorption and a reduced content of octahydrophenazine, but also the acid consumption is kept as low as possible.

We have found that this object is achieved by a process for preparing caprolactam by Beckmann rearrangement of cyclohexanone oxime with oleum at from 85° to 125° C. in a plurality of rearrangement stages arranged in series, wherein a portion of the reaction mixture leaving the last rearrangement stage is returned to at least one of the preceding rearrangement stages.

The novel process has the advantage that the quality of the caprolactam is improved in a straight-forward manner with, in particular, low levels being achieved for the permanganate titration number, the UV absorption and the octahydrophenazine content. The novel process has the further advantage that this is achieved with a reduced oleum consumption, which means that the unavoidable production of ammonium sulfate in the preparation of caprolactam is reduced.

As a rule, the cyclohexanone oxime is molten, e.g. is at from 80° to 95° C. The water content of the molten cyclohexanone oxime is, as a rule, from 1 to 7% by weight, in particular from 3.5 to 6% by weight.

The rearrangement is carried out in a plurality of rearrangement stages, e.g. 2 to 4 stages, arranged in series. The reaction is carried out in a mixture of caprolactam and oleum in these. The rearrangement stages can be designed as stirred tanks, but it is advantageous for the mixture of caprolactam and oleum to be circulated in each stage. Molten cyclohexanone oxime and, separately, oleum are fed in through distributors. Cyclohexanone oxime is added in each stage in the process according to the invention, advantageously in amounts which decrease from stage to stage, while at least 70% by weight, in particular at least 90% by weight, preferably the total amount of oleum required is fed into the first stage. It has proven advantageous to add from 60 to 85 parts by weight of cyclohexanone oxime and all the oleum in the first rearrangement stage, and to feed the remaining amount in decreasing ratio into the further rearrangement stages.

In the individual circulations it is expedient to circulate from 40 to 150 times the circulating volume per hour. The temperature is maintained at from 85° to 125° C., in particular from 95° to 120° C., by cooling. It has proven advantageous to increase the temperature by from 5° to 15° C. from stage to stage. For example, the first stage is kept at from 95° to 103° C., the second is kept at from 103° to 110° C. and the third at from 110° to 118° C.

As a rule, the oleum used has an $SO_3$ content of from 24 to 34% by weight, advantageously from 27 to 32% by weight. The reaction mixture in the individual stages is essentially composed of caprolactam, sulfuric acid, $SO_3$, decreasing amounts of unreacted cyclohexanone oxime and small amounts of undefined byproducts.

It is advantageous in a three-stage process to maintain an acid number of from 115 to 125 in the first stage, of from 105 to 112 in the second stage and of from 102 to 105 in the third stage. The acid number, expressed as the number of mEq of $H_2SO_4$ per 10 g of reaction mixture, was determined by titration.

The holdup time in each rearrangement stage is advantageously maintained at from 10 to 60 minutes.

A mixture essentially composed of caprolactam, sulfuric acid and a small amount of $SO_3$ is continuously removed from the last rearrangement stage at the same rate as cyclohexanone oxime and oleum have been fed into the preceding stages.

An essential feature of the present invention is that a portion, e.g. from 5 to 40% by volume, of the reaction mixture taken from the last stage is returned to at least one of the preceding rearrangement stages. With circulations it has proven particularly advantageous to return from 5 to 35% by volume, in particular from 10 to 30% by volume, of the circulating volume per hour, i.e. the amount circulated each hour in the last rearrangement stage, from the last rearrangement stage to the preceding stages. The portion of the reaction mixture which is to be returned is advantageously returned to the penultimate rearrangement stage.

Caprolactam is obtained from the rearrangement mixture as follows, for example: the resulting mixture, which is essentially composed of caprolactam, sulfuric acid, residual sulfur trioxide and byproducts, is neutralized with ammonia. The reaction mixture in a circulation system is advantageously fed into a 35-45% by weight aqueous ammonium sulfate solution and mixed with the latter, and gaseous ammonia is passed in until the pH is from 4 to 5. The crude lactam which now separates out is separated from the saturated ammonium sulfate solution, e.g. by decantation, and extracted with benzene or toluene. The extractant is removed and then the caprolactam is purified by distillation under reduced pressure.

The caprolactam obtainable by the process according to the invention is distinguished by greater purity and is suitable for preparing polycaprolactam for fibers. The process of the invention is illustrated by the following examples:

COMPARATIVE EXAMPLE

Three-Stage Rearrangement Without Return

In a circulation system of capacity about 5 l and composed of 3 mixing circulations, connecting lines, pumps, coolers and an overflow vessel, about 150 times the circulating volume was circulated in each mixing circulation. The amount of oleum required for the rearrangement was introduced via a distributor into the first mixing circulation. The amount of oxime was introduced into the 1st, 2nd and 3rd mixing circulations in the ratios 80:15:5 by weight.

The cyclohexanone oxime used had a water content of 4.2% by weight. The oleum had a free $SO_3$ content of 32%. The ratio by weight of oleum to oxime was 0.93:1.

The average holdup time in the circulating system was about 23 minutes. The individual mixing circulations were at 100°, 105° and 115° C. The free $SO_3$ content measured in the rearrangement mixture in the 3rd stage was 4.8%.

The amounts introduced into the three-stage reaction circulation are removed from the circulation as reaction product in the overflow vessel and are neutralized with ammonia or ammonia solution to a pH of 4.6. The crude lactam which separates out is separated off and prepurified in a conventional manner by extraction and subsequent distillation under reduced pressure.

The extracted lactam had the following characteristics:

| PTN (permanganate titration number) | | 19 |
|---|---|---|
| Extinction | 290 nm/10/50 | 6.1 |
| Octahydrophenazine | ppm | 0.8 |
| Volatile bases | mEq/kg | 0.7 |
| Impurities detectable by gas chromatography | ppm | 373 |
| Residual oxime content | ppm | 5 |

EXAMPLE 1

Procedure with Return, 3-Stage Rearrangement

The cyclohexanone oxime is rearranged in 3 stages in the same circulation system as described in the Comparative Example under the conditions indicated for that.

The oleum is fed into the 1st stage, while the cyclohexanone oxime is fed into the 1st, 2nd and 3rd mixing circulations in the ratios 80:15:5.

About 20% of the circulating volume per hour was returned from the 3rd stage to the 2nd rearrangement stage.

The content of free $SO_3$ in the rearrangement mixture leaving the 3rd mixing circulation was 4.9%.

The acid number was 118 in the first stage, 106 in the second stage and 104.5 in the third stage.

The final rearrangement mixture is worked up as described. The extracted lactam has the following characteristics:

| PTN | | 16 |
|---|---|---|
| Extinction | 290 nm/10/50 | 5.2 |
| Octahydrophenazine | ppm | 0.5 |
| Volatile bases | mEq/kg | 0.5 |
| Impurities detectable by gas chromatography | ppm | 133 |
| Residual oxime content | ppm | <1 |

To determine the PTN, 100 g of caprolactam were dissolved in 250 ml of 50% by weight sulfuric acid at 20° C. and treated with 0.1N potassium permanganate until a stable pink color was produced. The PTN is equivalent to the number of ml of potassium permanganate solution used, multiplied by 10 (i.e. based on 1 kg of caprolactam).

We claim:

1. A process for preparing caprolactam by Beckmann rearrangement of cyclohexanone oxime with oleum at from 85° to 125° C. in a plurality of rearrangement stages arranged in series, which comprises returning a portion of the reaction mixture leaving the last rearrangement stage to at least one of the preceding rearrangement stages.

2. A process as claimed in claim 1, wherein 2 or 3 rearrangement stages are applied.

3. A process as claimed in claim 1, wherein from 10 to 30% of the circulating volume per hour is returned from the last rearrangement stage to at least one of the preceding rearrangement stages.

4. A process as claimed in claim 1, wherein reaction mixture is returned from the last rearrangement stage to the immediately preceding rearrangement stage.

* * * * *